United States Patent [19]

Bogusiewicz et al.

[11] Patent Number: 5,427,096
[45] Date of Patent: Jun. 27, 1995

[54] WATER-DEGRADABLE ELECTRODE

[75] Inventors: Valentine Bogusiewicz, Plymouth; Cydney A. Einck, Edina, both of Minn.

[73] Assignee: CMC Assemblers, Inc., Hopkins, Minn.

[21] Appl. No.: 157,896

[22] Filed: Nov. 19, 1993

[51] Int. Cl.[6] ............................................. A61B 5/04
[52] U.S. Cl. ..................................... 128/639; 128/640; 128/641; 607/149; 607/152
[58] Field of Search ............... 128/639, 640, 641, 644; 607/149, 152, 153

[56] References Cited

U.S. PATENT DOCUMENTS

| | | |
|---|---|---|
| 3,752,151 | 8/1973 | Robichaud . |
| 3,865,099 | 2/1975 | Robichaud . |
| 3,882,853 | 5/1975 | Gofman et al. . |
| 3,976,055 | 8/1976 | Monter et al. . |
| 4,066,078 | 1/1978 | Berg . |
| 4,267,840 | 5/1981 | Lazar et al. . |
| 4,270,544 | 6/1981 | Gilden et al. . |
| 4,352,359 | 10/1982 | Larimore et al. . |
| 4,370,984 | 2/1983 | Cartmell . |
| 4,481,167 | 11/1984 | Ginter et al. . |
| 4,516,581 | 5/1985 | Sessions . |
| 4,602,640 | 7/1986 | Wada et al. . |
| 4,628,944 | 12/1986 | MacGregor et al. . |
| 4,657,023 | 4/1987 | Kuhn . |
| 4,674,511 | 6/1987 | Cartmell . |
| 4,679,563 | 7/1987 | Wada et al. . |
| 4,679,564 | 7/1987 | Sessions . |
| 4,685,467 | 8/1987 | Cartmell et al. . |
| 4,694,835 | 9/1987 | Strand . |
| 4,848,348 | 7/1989 | Craighead . |
| 4,852,571 | 8/1989 | Gadsby et al. . |
| 5,042,144 | 8/1991 | Shimada et al. ............... 128/641 |
| 5,337,748 | 8/1994 | McAdams et al. ............. 607/152 |

FOREIGN PATENT DOCUMENTS 9300857 1/1993 European Pat. Off. ............ 128/640

OTHER PUBLICATIONS

CYA Products, Inc., Products Advisory, Jul. 2, 1992.

*Primary Examiner*—Krista M. Pfaffle
*Attorney, Agent, or Firm*—Merchant, Gould, Smith, Edell, Welter & Schmidt

[57] ABSTRACT

A water-degradable electrode, its method of preparation and a method or reclaiming valuable metal or metal alloy from such water-degradable electrode after use are provided. The water-degradable electrode contains a water-degradable, electrically nonconductive substrate and a nonphotosensitive, electrically conductive layer containing a metal or metal alloy. The metal- or metal-alloy-containing, nonphotosensitive, electrically conductive layer is disposed on the water-degradable nonconductive substrate. After the electrode has been used, the nonphotosensitive, electrically conductive material can be reclaimed by degrading in water the electrically nonconductive substrate on which the conductive material is disposed.

21 Claims, 2 Drawing Sheets

WATER-DEGRADABLE ELECTRODE

FIELD OF THE INVENTION

The present invention relates to an electrode for monitoring electrical signals from a mammalian body or for electrically stimulating such a mammalian body.

BACKGROUND OF THE INVENTION

Electrodes are widely used in the biomedical environment. They can be used for electrically stimulating a patient and/or monitoring of electrical signals of the patient. Generally, electrodes are applied on human beings, although they can be used on other mammals, such as dogs, cats, horses, and the like. A mammalian body generates many different electrical signals. The monitoring of these signals can provide valuable diagnostic information for the medical practitioner on the physiological functions of the patient generating the signals. Electromyograms (EMG), electrocardiograms (ECG) and electroencephalograms (EEG) are examples of records of commonly monitored electrical physiological signals. In addition, sometimes it is necessary to stimulate an individual to promote physiological activity. For example, muscle groups may need to be stimulated. In some patients, the rhythm of the heart may have to be controlled by a pacemaker. In other patients, there may be a tendency to undergo cardiac fibrillation, in which case prompt defibrillation by controlled electrical shocks to the heart is critical for the survival of the patient.

To obtain effective electrical connection between an electrode and the surface of a mammalian body, it is necessary to establish good contact between the electrode and the surface. For example, in the monitoring of an ECG, the electrode is attached to the skin by means of an electrically conductive adhesive. Alternatively, an electrically conductive paste, cream, or gel is disposed between the skin and the surface of the electrode. In such a case, the electrode may have to be secured in place by adhesive tape or the like.

An electrode suitable for monitoring physiological signals or stimulating physiological activities typically contains an electrically nonconductive layer (or substrate) and an electrically conductive layer disposed on the substrate.

A relatively expensive metal is often used for signal sensing or electrical current dispersion and is sandwiched or interposed between the nonconductive substrate and the conductive adhesive. After an electrode has been used, it often must be disposed of or discarded. Even in the case of reusable electrodes, after a period of use, an electrode may become functionally impaired and is no longer useable. Disposal of such electrodes without recycling represents a loss of a material that has significant economic value. Furthermore, the disposal of such electrodes, which may contain metals such as silver, copper, and the like, often results in pollution. Metals such as copper and silver, if not properly disposed of, may leach out of the electrodes and contaminate the environment. Therefore, it is preferable that the electrodes be recyclable, i.e., the metals be reclaimable from the electrodes after the electrodes are used.

In conventional electrodes, an electrically conductive material, usually a metal, is bonded to an electrically nonconductive material, usually a water-insoluble polymeric material. Any effort to recycle the electrode faces the problem of economically separating the metal from the polymeric material.

Cartmell (U.S. Pat. No. 4,674,511) discloses a medical electrode which may be x-ray transparent. The medical electrode contains a thin layer of a conductive paint adhered to a thin supporting substrate. A first area of the conductive material is adapted for contacting an electrolyte used to bridge the conductive material to the skin. A second area of the conductive material is provided for connection of an electrode to external equipment. A silver paint is described as preferably applied by silk-screening. Conductive adhesives are also described to be applicable over the conductive layer.

Monter, et al. (U.S. Pat. No. 3,976,055) disclose an electrode for monitoring signals such as electrocardiographic signals. The electrode has a conductor containing a first galvanically inactive material and a second galvanically active conductive material. The first conductive material may contain a plastic body formed from a nonconductive binder made conductive by inclusion of electrically conductive carbon disbursed therein. Metallic particles may also be incorporated into the electrode to improve performance.

Berg (U.S. Pat. No. 4,066,078) discloses a disposable electrode for use in medical applications including monitoring and stimulation. The electrode contains a conductive member which may be a pliable sheet of material. A material having adhesive properties is provided to assist the adherence of the electrode to the skin. Suitable electrically conductive organic polymers for providing an adhesive composition are also disclosed.

Larimore, et al. (U.S. Pat. No. 4,352,359) disclose a disposable biomedical electrode. The biomedical electrode contains an electrically conductive material on the body-contacting surface. The electrically conductive material has a dermally non-irritating, conformable, cohesive, synthetic, hydrophilic polymer. In one preferred embodiment, an electrical connector stud extends from an electrode plate which is in contact with the conductive material. The polymeric material in the conductive material has at least five or more percent of monomer units containing a salt of a carboxylic acid. The possibility of electrodes containing electroplates of silver or nickel are disclosed.

Gadsby et al. (U.S. Pat. No. 4,852,571) disclose a disposable, biopotential electrode having a plastic base, a layer of carbon, a layer of silver-silver chloride and an electrically conductive adhesive.

SUMMARY OF THE INVENTION

The present invention addresses the need for a recyclable electrode, particularly an electrode from which metal or alloy can be reclaimed easily and economically without the use of organic solvents that may pollute the environment. The present invention is a water-degradable electrode that comprises a water-degradable, electrically nonconductive substrate and a nonphotosensitive, electrically conductive layer containing a metal or metal alloy disposed on the nonconductive substrate. The water-degradable electrode can be used for contacting and conforming to a mammalian body surface to electrically stimulate or monitor such a mammalian body. The present invention is also directed to a method of making, and a method of recycling such a water-degradable electrode by reclaiming the valuable metal or metal alloy from a used electrode.

In the present invention, the metal- or metal-alloy-containing, nonphotosensitive, electrically conductive layer is disposed on the water-degradable nonconductive substrate. The electrically conductive layer is nonphotosensitive in that its electricity conducting property is unimpaired upon exposure to light (e.g., visible light, UV light, or X-ray) as well as in darkness. Thus, the electrode will function properly regardless of light illumination.

The water-degradable electrode is useful for biological and medical applications such as the monitoring of electrical signals from the skin of an individual and/or for stimulating purposes. Typical monitoring applications include the monitoring and recording of signals such as EEG, ECG, EMG, and the like. Stimulating purposes include, for example, the stimulation of muscular activities, TENS (transcutaneous electrical nerve stimulation), and particularly, controlling the heart beats of an individual or defibrillating a fibrillating heart. The term "water-degradable" refers to the capacity to undergo disintegration or deterioration in an aqueous solution. The aqueous solution may contain, in dilute concentration, pH-adjusting chemicals and enzymes.

The water-degradable nonconductive substrate typically is or comprises a polymeric material selected from the group consisting of polyvinyl alcohol, polysaccharide, polypeptide, polylactide, polyglycolide, polycaprolactone, polyvinylpyrollidone, polyanhidride, polyacrylamide, as well as any combination thereof. It is preferable that the water-degradable nonconductive substrate is or comprises a water-soluble material, preferably polyvinyl alcohol or polyvinylpyrollidone. It is also practicable to use as the substrate a material that may not be very water-soluble, but tends to deteriorate or disintegrate in water, particularly in acidic or alkaline condition and/or with the aid of enzymes. Examples of such materials are polylactides, polyglyocolides, polycaprolatones, polysaccharides such as starches, and polypetides.

The nonphotosensitive, electrically conductive layer can contain a metal or metal alloy. The metal or metal alloy may constitute the entire conductive layer, or it may be part of a material that composes the layer. For example, the layer may contain metallic particles bound by and dispersed in a resin such as polyvinylchloride, polyethylene, silicone rubber, or an ethylene vinyl acetate copolymer (see, e.g. Monter et al., U.S. Pat. No. 3,976,055). Examples of suitable metal or alloy include gold, platinum, silver, copper, aluminum, nickel, tin and stainless steel. Because of its moderate pricing and high electrical conductivity, silver is the preferred metal for making the electrode. More preferably, the electrode comprises a mixture of silver and silver chloride. The layer of nonphotosensitive, electrically conductive material can be a solid, homogenous, metal or metal alloy layer, or it can be composed of nonphotosensitive, electrically conductive particles embedded or dispersed in a nonconductive material such as a resin. In addition, nonmetallic, electrically conductive, galvanically inactive materials such as carbon can also be incorporated in the layer of nonphotosensitive, electrically conductive material. Optionally, an additional layer of a nonmetallic, electrically conductive, galvanically inactive material, e.g., carbon, can be disposed between the substrate and the layer of nonphotosensitive, electrically conductive material containing a metal or metal alloy.

Typically, a water-degradable electrode of the present invention contains an electrically conductive pressure sensitive adhesive that is disposed on the layer of nonphotosensitive, electrically conductive metal- or metal-alloy-containing material. An electrically conductive paste, cream, or gel can also be used instead of the pressure sensitive adhesive. Further, in some applications, it is preferable that neither an adhesive, cream, paste nor gel be used. In such an instance, the electrode can be applied to the skin of a patient and secured in place by means of pressure sensitive adhesive tape or the like. The pressure sensitive adhesive, paste, cream, or gel can also be water-soluble or water-degradable.

After the water-degradable electrode has been used and is to be discarded, it can be recycled. The electrode can be immersed in an aqueous solution, e.g., tap water, and the adhesive can be dissolved in the aqueous solution. In the cases where the pressure sensitive adhesive is made of a material that is not readily soluble or may take a relatively long time to disintegrate, the pressure sensitive adhesive can be peeled from the electrode before the electrode is placed in the aqueous solution. The insoluble metal- or metal-alloy-containing material can be separated by mechanical methods such as precipitation, filtration and centrifugation. The metal in the metal- or metal alloy-containing material can be further purified from the precipitate by chemical means such as leaching or electroplating. Such chemical purification methods are known in the art.

DETAILED DESCRIPTION OF THE INVENTION

The present invention is an electrode that comprises a water-degradable, electrically nonconductive substrate and a nonphotosensitive, electrically conductive layer containing a metal or metal alloy disposed on the nonconductive substrate and is preferably conformable to the contour of the surface of a mammalian body. As used herein, an electrode is "conformable" to the contour of the mammalian body if the substrate is flexible, thin, and/or soft enough that when applied, 90% or more of the body-contacting surface of the electrode is in contact with the mammalian body surface, e.g. the forehead, shaved scalp, chest, back, or thigh of a person.

Water-Degradable Nonconductive Substrate

The purpose of the nonconductive substrate of this invention is to provide physical and mechanical integrity to the electrode as well as to insolate one side of an electrode to minimize unintended contacts with the conductive parts of the electrode. Because the surface of a mammalian body may be, and usually is, curved, an electrode preferably has sufficient flexibility to enable the contacting surface to conform to the contour of the target area on the mammalian body. Therefore, the substrate is preferably made of a somewhat flexible material of suitable thickness to provide the required flexibility. It is preferable that the substrate be flexible enough such that it can be rolled into a cylindrical roll with 1 cm diameter without cracking or otherwise losing its mechanical integrity.

The water-degradable nonconductive material used to form the substrate is one which can be fabricated with dimensions to maintain mechanical and electrical integrity during fabrication, storage and use of the electrode. The appropriate dimension depends on the particular application of the electrode and the polymeric material selected. For example, if the electrode is to be applied on a patient's forehead for a few minutes only, a relative thin and small substrate (e.g., 0.05 mm×2 cm×3 cm) may be adequate because it is unlikely that the electrode will detach from the skin of the patient or that the substrate will deteriorate during use. Based on the present disclosure and factors such as flexibility desired, location of application and whether the electrode is for monitoring or stimulation purpose, a person skilled in the art would be able to determine the appropriate dimensions for a particular application.

The substrate can be composed of a homogenous layer of a polymeric material or it can be a composite or blend of different materials. For example, the substrate can be a mixture of two or more water-soluble thermoplastic polymers. The nonconductive substrate can also contain materials that are not water-soluble as long as the substrate as a whole can be degraded or disintegrates in water so that the nonphotosensitive, electrically conductive material can be separated efficiently from the materials that compose the electrically nonconductive substrate.

Preferably, the electrically nonconductive substrate contains a water-soluble polymer. The term "water-soluble" refers to materials that can be dissolved in water of below 100° C. Typically, such materials have a maximum solubility in water of about 1 gram per liter or more. In some cases, pH-adjusting chemicals such as acids and alkalis can be added to the water to assist the solubilization. Generally, a dilute concentration of less than about 0.5 Mole per liter of a pH-adjusting chemical is preferred. Representative examples of water-soluble polymers include polyvinyl alcohol, polyvinyl pyridine, polyacrylamide, polyvinylpyrrolidone, polyethylene oxide, gelatinized starch, and gelatin. Generally, such water-soluble materials disintegrate in water of suitable temperature (e.g. 50° C.) and pH within a few hours and any insoluble material that is bonded to a substrate of such water-soluble materials can be recovered by mechanical separation methods such as centrifugation or filtration.

Other materials that are commonly considered water-insoluble can also be used for forming the substrate. For example, there are polymers that tend to disperse or disintegrate in water over a period of time longer than a few hours. Another example is a substrate made with water soluble polymer with water-insoluble fibers (e.g., cellulosic fibers or nylon fibers) embedded therein for strength. However, such materials, under the appropriate pH and temperature conditions, can be softened to an extent that allows for the separation of the nonphotosensitive, electrically conductive material from the electrically nonconductive material. For example, the polymeric, electrically nonconductive material can become gel-like and thus can be disrupted mechanically from the electrically conductive metal- or metal-alloy-containing material. The nonphotosensitive, electrically conductive material, if made to have a higher density than this gel-like material, or have different shapes and dimensions, can be separated from the disrupted gel-like material by centrifugation and/or filtration. In an embodiment wherein the conductive layer remains a solid layer in water, the conductive layer can be easily separated from any fibrous material or pieces of disrupted substrate resulting from the disintegration of the substrate.

The preferred water-degradable polymer is polyvinyl alcohol (PVA). Commercially available PVA useful for making the present invention generally has a nominal molecular weight of about 20,000 to about 100,0000, preferably about 80,000 to about 300,000, and most preferably about 100,000 to about 120,000. PVA is available, for example, as VINOL TM from Air Products, Inc., as ALVANOL TM from E. I. du Pont de Nemours & Co. (Wilmington, Dela.), and as GELVITOL TM from Monsanto Co. (St. Louis, Mo.), and water dissolvable paper from Custom Papers Group Inc. (Richmond, Va.). Representative examples of useful water dissolvable paper from Custom papers Group Inc. are 120FD, 60FD, 30FD, 60SD, and 30SD water dissolvable papers.

Also useful as the water-degradable polymer of this invention is polyvinylpyrrolidone (PVP) of molecular weight of about 10,000 to about 360,000, although the preferred molecular weight is about 30,000 to 100,000. PVP with molecular weight of about 10,000, 40,000 and 360,000 (K value (intrinsic viscosity) of 12–18, 28–32, and 80–100, respectively) can be obtained from Sigma Chemical Co., St. Louis, Mo. The most preferred PVP has an average molecular weight of about 55,000 and a K value (intrinsic viscosity) of about 30, e.g., PVP K-30 from International Special Products, Lombard, Ill.

For the determination of characteristics of polymers, such as molecular weights, K valves and the like, the methods used by the commercial suppliers of these polymers are herein incorporated by reference.

Gelatin can also be used as the water-degradable polymer for making the electrically nonconductive, water soluble substrate. An example is type A gelatin of 300 bloom from swine skin.

Other materials that are water-degradable and can be used for forming a substrate of the present invention, are, for example, polysaccharides, polypeptides, polylactides, polyglycolides, polycaprolactones, polyanhydrides, polyacrylamide, and copolymers and mixtures thereof. The degree of water degradability of the above-mentioned polymers is dependent on molecular weight. Usually, for a polymer of the type described above, the lower the molecular weight, the more water-soluble or water-degradable it is. However, a polymer with lower molecular weight usually forms a solid that is less firm and has less mechanical integrity and therefore can be damaged with less mechanical force. In the selection of a water-degradable polymeric material, it is desirable to balance the need for mechanical strength and water degradability.

Some polymers useful in fabricating the electrically nonconductive substrate of this invention, particularly biological polymers, such as polysaccharides and polypetides, can be degraded by enzymes. For example, starches can be degraded under suitable conditions of temperature and pH by amylases. Polypetides, including proteins, can be degraded by suitable proteases. Cellulose can be degraded by cellulase. When a material degradable by enzymatic activities, such as a starch or a protein, is used for forming the substrate, the rate of degradation of the substrate can be increased by using an effective amount of an appropriate enzyme under suitable temperature and pH conditions.

The substrate can also contain other materials that improve the property of the substrate or facilitate the process for the formation of the substrate. For example, stabilizers can be incorporated into the polymeric materials to extend the life of the polymer. Plasticizers can be incorporated to increase the flexibility of the polymeric material. Surfactants can also be used in a composition for making the substrate so that a uniform layer of the composition can be applied to a surface to form a substrate layer. It is also not necessary that the substrate be a homogenous layer. There may be particles, fibers, and the like present to improve the physical strength and flexibility of the substrate. Other optional components that can be incorporated in the substrate are, for example, pigments, and fillers.

Depending on the particular polymeric material selected for making the substrate, the size and shape of the electrode, the flexibility and the mechanical strength desired, the thickness of the substrate can vary. Preferably, when polymer such as PVA or PVP is used in the substrate, the thickness of the substrate made therefrom is about 0.05 mm to about 2 mm, more preferably about 0.1 mm to about 1 mm, and most preferably about 0.1 mm to about 0.2 mm (0.004 inch to 0.008 inch). For other substrates, a thickness outside these ranges may be preferred. For example, for relatively nonflexible and fragile materials such as gelatin or gelatinized starch, a thicker layer (e.g. about 2 mm to about 5 mm) may be preferred. Such thick substrates may be formed by casting a solution of the polymer on a surface, allowing it to dry (i.e., allowing the liquid to evaporate so that a solid layer remains) and then repeating the process of casting the solution on top of the dried polymeric layer and drying until the desired thickness is obtained. Depending on the particular polymer used and the thickness of the solid substrate desired, the concentration of the polymer in the casting solution can vary. For a thick substrate (e.g., about 2 mm), a more concentrated solution is preferred, as long as the polymer remains soluble and the solution is not too viscous to flow and spread on a flat surface.

Nonphotosensitive, Electrically Conductive Material

A metal or metal alloy that is electrically conductive and has the physical and the mechanical integrity necessary for the function of an electrode can be used for forming the nonphotosensitive, electrically conductive layer.

Generally, electrodes of this invention can be fabricated for use for monitoring, diagnosing and stimulating purposes. For monitoring or diagnostic purposes, metal or metal alloy that has the desired electrical conductivity, mechanical strength and integrity as an electrode can be used. Examples of suitable metals and alloys include gold, platinum, copper, aluminum, nickel, tin, zinc, stainless steel and the like. The choice of the particular metal or metal alloy depends on many factors, such as electrical conductivity, mechanical strength, cost, and chemical inertness. Based on their chemical inertness and/or relatively high electrical conductivity, precious metals such as gold, platinum, silver, and the like are preferred. Because of its high electrical conductivity and moderate cost, silver is particularly preferred. In electrodes that are used primarily for monitoring and diagnostic purposes, the layer of nonphotosensitive, electrically conductive material can be a homogenous layer of metal or metal alloy.

In electrodes of this invention that are used for stimulating purposes, such as muscular stimulation and cardiac defibrillation, the electrically conductive material layer containing only a homogenous metal may not be entirely suitable. For example, in an defibrillating electrode, the electrical current can be discharged more effectively from an electrode that contains a mixture of silver and silver chloride (hereinafter "silver-silver chloride") than from a metallic layer that is pure silver. Therefore, an electrically conductive layer containing silver-silver chloride is preferably used in electrodes used for stimulating purposes. However, such silver-silver chloride electrodes can also be used for monitoring and diagnostic purposes. Commonly known methods in the art can be used for making silver chloride from silver. For example, silver can be reacted with hydrochloric acid, an aqueous chlorine solution, or a strong oxidizing alkaline agent such as sodium hypochlorite to form silver chloride. Such methods can be used to form silver chloride on a layer of silver.

The nonphotosensitive, electrically conductive layer of the electrode of this invention can also be formed by incorporating particles of silver or silver-silver chloride in a nonconductive binder, as long as the conductive particles are numerous enough to render the whole layer electrically conductive. Conductive but nonmetallic, non-galvanically active materials can be incorporated into the layer. For example, carbon particles and silver-silver chloride particles can be embedded in a nonconductive binder (e.g., a resin) to form the nonphotosensitive, electrically conductive layer. A nonphotosensitive, electrically conductive layer can also be made by forming a layer from a non-metallic, non-galvanically active material (e.g. carbon particles) and binder and then disposing a thin layer of a nonphotosensitive, electrically conductive, metal- or metal-alloy-containing (such as silver-silver chloride) material on the electrically conductive layer containing the nonmetallic, non-galvanically active material.

When the present nonphotosensitive, electrically conductive layer is relatively hard or rigid, such as a metal or metal alloy layer, this layer can be bonded to the substrate by an adhesive. Commonly available adhesive can be used, while water-soluble adhesives are preferred. However, other means can be employed for forming the present nonphotosensitive, electrically conductive layer on the substrate. For example, a layer of ink containing the suitable metal or metal alloy particles (e.g. gold-containing paint, silver-containing ink or silver-and-silver-chloride-containing ink) can be applied to the surface of the substrate by techniques such as silk-screening, printing (e.g., flexographic printing), brush painting, or spray painting. Such inks as well as silver- or silver-and-silver chloride-containing paints are known in the art and are commercially available. Such ink or paint usually contains binders for binding the silver and silver chloride particles to a surface to which the ink or paint is applied. An example of a suitable silver-and-silver-chloride-containing ink (hereinafter "silver-silver chloride ink") is SS-24633 available from Acheson Colloids, Port Huron, Mich. Another supplier of such silver-silver chloride ink is Olin Hunt, Ontario, Calif. Other suitable methods for forming the present nonphotosensitive, electrically conductive layer on the surface of a substrate are, for example, gravure printing, sputter coating, and dipping. Electroplating can also be used to form a metal layer on a conductive surface. Such methods are well known in the art.

When a non-metallic, non-galvanically active material such as carbon particles is incorporated along with the metal or metal alloy particles into the nonphotosensitive, electrically conductive layer of this invention, it is preferable that the nonmetallic, galvanically inactive particles are of different sizes from the metal or metal alloy particles. This difference in size facilitates the separation of the metal or metal alloy particles in the recycling effort.

The aforementioned method of coating with a metal- or metal-alloy-containing ink can also be used to coat a hard or relatively rigid substance such as plastic, metal or metal alloy layer with a preferred nonphotosensitive, electrically conductive coating such as a silver-silver chloride ink to form the nonphotosensitive electrically conductive layer. If such a relatively rigid electrically conductive layer is used, preferably a relatively soft, conformable, electrically conductive adhesive layer is disposed on the relative rigid electrically conductive layer such that the electrode has a contacting surface that conforms to the contour of the mammalian body. The rigid substance can also be a water-degradable substance, such as those described hereinabove.

The nonphotosensitive, electrically conductive layer preferably has a thickness effective to provide the electrical conductivity and physical integrity needed for the intended application while permitting enough flexibility to enable conformity to the contour of the target area. When a silver-silver chloride layer is coated on the substrate, the thickness of the silver-silver chloride layer is typically about 0.01 mm to about 0.2 mm, preferably about 0.05 mm to 0.1 mm.

Adhesive

For securing the electrode of the present invention to a surface of a source of electrical signals, for example the skin of a person, an electrically conductive adhesive can usually be employed. Such an electrically conductive adhesive can contain natural polymers such as polysaccharides or synthetic polymers. The adhesive can be rendered electrically conductive by the incorporation of certain metal cations, for example, sodium, potassium, calcium or magnesium. Examples of polysaccharides that are suitable for use as adhesives are gums such as xanthan gum, gum arabic, gum karaya, and the like.

Many synthetic polymers are suitable for use as the pressure sensitive adhesive used in this invention. To be suitable as an adhesive for use on an electrode in direct contact with skin, it is preferable that the adhesive be dermally non-irritating, cohesive, film-forming, hydrophilic, and water-soluble. Examples of synthetic polymers that are suitable for use as pressure sensitive adhesives in an electrode are polyacrylic acids, and copolymers of acrylates and acrylic acid. In such electrically conductive adhesives, typically cations such as alkali metal ions, ammonium ions and alkaline earth metal ions are used for rendering the adhesive electrically conductive. Examples of electrically conductive adhesives are disclosed by Berg (U.S. Pat. No. 4,066,078), Lazer et al. (U.S. Pat. No. 4,267,840), and Wada et al. (U.S. Pat. No. 4,602640).

It is preferable that the adhesive layer be cohesive enough that it can be peeled from the substrate and from the nonphotosensitive, electrically conductive metal or metal alloy containing layer without removing the non- photosensitive, electrically conductive metal- or metal-alloy-containing layer from the substrate.

It is also preferable that the adhesive be water-degradable, more preferably, water-soluble such that any adhesive that has not been peeled off can be dissolved in water. In this way, the nonphotosensitive, electrically conductive material can be recovered with ease.

Many water-soluble, electrically conductive adhesives are commercially available. Examples are PROMEON hydrogels such as PROMEON RG63B, RG63G, and RG63X available from Promeon Division of Medtronic, Inc., Minneapolis, Minn., and LECTEC membranes such as LECTEC 4,000 available from LECTEC Corp., Minnetonka, Minn.

The electrode of the invention can be made so that it can be applied to the skin of a patient without an adhesive. Electrically conductive paste, cream, or gel which have been used in the art for providing good contact between the electrode and the skin surface can be used to apply the electrodes of this invention. Such paste, cream, or gel are particularly applicable when the contour of the skin surface is not flat and therefore difficult to maintain good contact between the electrode and the skin. In such a case, the electrode can be held in place by tape or other means of securing the electrode to the skin. Sometimes the application of an adhesive layer, paste, cream or gel are not desirable. In patients with contagious diseases, the adhesive layer, paste, cream or gel may tend to harbor pathogens. In such cases, it may be preferable to apply the electrode with the nonphotosensitive, electrically conductive, metal- or metal-alloy-containing layer in direct contact with the skin. Again, the electrode can be secured to the skin by means of adhesive tape or the like.

Preparation of the Electrode

The water-degradable substrate of the present invention can be made by forming a film of the water-degradable material and cutting out a piece of the appropriate dimensions. For example, a solution of a water-soluble polymer can be cast on a surface and allowed to dry to form a film of desired thickness. From information available from the manufacturer, the concentration and condition for casting a film can be determined without undue experimentation. For example, water soluble PVA papers such as 120FD, 120SD, 60FD, 60SD obtainable from Custom Papers Group, Inc., Richmond, Va. (polyvinyl alcohol of molecular weight of about 100,000 to 120,000), can be dissolved in water to form a 5 wt % solution at 30° C. and cast on a flat surface and allowed to dry to form a film of about 0.1 mm thickness. Similarly, PVA of average molecular weight 30,000–70,000 and average molecular weight of 70,000–100,000 (Sigma Chemical Company Product No. P 8136 and P1763 respectively) can be used in an analogous manner. Alternatively, commercially available water-degradable films, such as the aforementioned water soluble papers can be cut to the desired size and shape for use as substrate in the present invention.

Generally, electrodes of the present invention can be made by laminating the water-degradable substrate, the electrically conductive, metal- or metal-alloy-containing layer, and, optionally, the adhesive layer together. In some cases, a thin, flexible electrode can be made by depositing a thin electrically conductive, metal- or metal-alloy-containing layer such as a silver-silver chloride layer directly on the substrate with techniques such as, e.g. flexographic printing, silkscreening, and brush painting.

In other cases, wherein the electrically conductive layer is formed by coating a hard or relatively rigid substance such as a metal, or plastic with a desired electrically conductive substance such as a silver-silver chloride layer, the hard or relatively rigid substance can be formed to have a male snap-fastener for snap-fitting with a wired, female snap-fastener for connecting to electrical devices such as monitors or defibrillators.

Another preferable way of making an electrode is to press an electrically conductive eyelet into an electrically conductive snap-fastener by perforating a water-degradable substrate, thus securing the snap-fastener, the substrate and the eyelet together. The eyelet can have a flat base member and can be coated with a desired electrically conductive material such as silver-silver chloride. Eyelets can be coated with silver-silver chloride by the aforementioned commonly used methods of coating. A preferred method of coating is to tumble an eyelet in a tumbler with a silver-silver chloride ink until the eyelet is completely covered with the ink and then allowing the eyelet to dry. Eyelets that have a layer of silver-silver chloride already coated thereon are also commercially available, for example, from Micron Medical Products, Inc., Fitchburg, Mass.

In the preferred embodiment in which an adhesive layer is provided in the electrode, preferably, a release liner (or a release-lined means) is used to protect the adhesive before use. The release liner can be disposed on the exposed surface of the adhesive layer of the electrode to form an electrode assembly. The preferred release liner has a surface with low surface energy for contacting the adhesive layer. Various release liners are known in the art. Typically, such a release liner is made by coating a thin plastic film or a sheet of paper with a release agent such as silicone or polytetrafluoroethylene (PTFE). Some release liners may be heat cured, UV cured, or electron beam (EB) cured. Preferably, the release liner is made by coating the release agent on a film such as paper, e.g. kraft paper; polyolefin film, e.g. polypropylene or polyethylene; polyester film, e.g. polyethylene terephthalate; or MYLAR. If desired, the release liner can be a homogeneous layer, preferably of plastic material, such as the above-mentioned plastics: polyolefin, silicone, or polyester. The preferred homogeneous release liner is a polyester or polyethylene film. The more preferred release liner is a silicone-coated polyester or polyethylene film.

In a preferred embodiment in which a release liner is used to protect the adhesive of the electrode and the adhesive layer has a larger surface area (i.e. planar dimension) than the electrically conductive metal- or metal-alloy-containing layer, to facilitate separating the adhesive from the release liner, preferably part of the adhesive layer on the electrode facing the release liner is covered with a thin nonadhesive film, such as paper. To use the electrode, a person can easily lift the release liner from the paper lined area of the adhesive layer and peel apart the release liner and the adhesive layer. If desired, to further facilitate separation of the release liner from the adhesive layer, each of the following: the substrate, the adhesive layer, and the release liner can be made to have a tab shaped piece extending from the circular layer. The tab shaped piece of the adhesive layer facing the release liner can be lined with paper.

Reclamation of Metal from the Electrode

After an electrode of the present invention has been used, it can be recycled by the reclamation of metal. First, the adhesive layer, paste, cream or gel can be removed from the electrode. The cream, paste, or gel can simply be wiped off, and the adhesive layer can be peeled from the electrode. Then the remaining nonphotosensitive, electrically conductive, metal- or metal-alloy-containing layer, as well as the substrate, can be placed in an aqueous composition suitable for degrading the water-degradable substrate. The aqueous composition can contain pH adjusting chemicals or other chemicals that tend to break down, soften, or dissolve the substrate. Examples of such chemicals that tend to promote the solubilization, softening, disintegration, and degradation of the substrate are acids, alkalis, and enzymes such as amylases and proteases and the like. In the cases in which the adhesive still adheres to the non-photosensitive, electrically conductive, metal- or metal-alloy-containing layer when the electrode is placed in the aqueous composition, if the adhesive is soluble in water, it can be removed by solubilization. If the adhesive is insoluble in water, it may be removed after the water-degradable substrate has been dissolved. In the instance where an aggressive adhesive which does not release in water the electrically conductive metal or metal alloy is used, the adhesive layer is preferably peeled from the electrode before the electrode is immersed in the aqueous solution to solubilize the substrate.

After the substrate has been adequately degraded, the nonphotosensitive, electrically conductive, metal- or metal-alloy-containing layer becomes separated from the disintegrated substrate. The valuable metal or metal alloy in the nonphotosensitive, electrically conductive layer may be separated by filtration. Sometime, the difference in density of the metal or metal alloy from the density of the material that composes the substrate may be significant enough that centrifugation can be used for separating the metal or metal alloy from the substrate material that has not been dissolved.

In the case wherein a pure metal is used for making the nonphotosensitive, electrically conductive, metal- or alloy-containing layer, the separation of the metal or metal alloy may be accomplished by simple filtration or centrifugation. In cases where an insoluble metal oxide, or metal salts such as silver chloride is present, the metal can be separated by chemical leaching, ion-exchange, electroplating and/or other chemical techniques. Such techniques are well known in the art.

In the preferred embodiment in which the valuable insoluble metal or metallic compound is silver and silver chloride, the silver and silver chloride can be recovered to provide an economic benefit to the recycler. In many modern institutions, such as hospitals, there are silver reclamation devices for extracting the silver from x-ray film processing streams. Such silver reclamation devices can be used for processing the silver-silver chloride material collected after dissolving the substrate. The silver-silver chloride, being insoluble, can be precipitated, collected and purified by chemical means. Such methods are known in the art and suitable conditions and procedures can be established by routine methods of experimentation. Once the silver and silver chloride particles are collected, they can be sold to commercial entities that process or manufacture silver products. An example of commercially available silver, silver chloride recovering system is CYA Effuluent Treatment System 32-04 SBS (CYA Products, Inc., Long Island City, N.Y.). Analogous methods can be used for reclaiming valuable insoluble substances such as gold particles in a gold-paint used in an electrode.

PREFERRED EMBODIMENTS

The following embodiments of the invention are specific examples which contain the best mode known to the inventors. These embodiments are presented merely for illustrative purposes and are not to be interpreted as limitations of the scope of the invention.

EXAMPLE 1

Electrode

Figure 1:
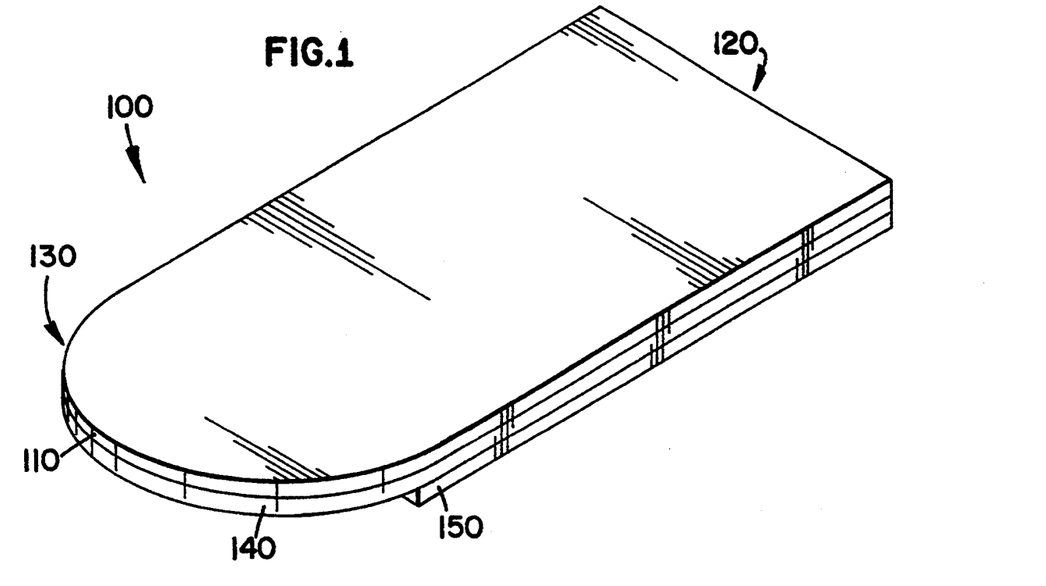
FIG. 1 is an isometric view of a preferred embodiment of a water-degradable electrode.

Referring to FIG. 1, the preferred embodiment was an electrode 100 that included a flexible, dimensionally stable substrate of polyvinyl alcohol (water soluble paper 120FD from Custom Papers Group, Inc. of Richmond, Va.) having a thickness of about 0.2 mm (8 mils). The electrode 100 had an elongated shape having two ends 120 and 130. The first end 120 was rectangular in shape while the second end 130 was circular in shape. The straight edge of the length of the substrate was about 2.5 cm long and the width was about 1.75 cm. The substrate was shaped by die cutting. A layer of silver-silver chloride ink SS-24633 (Acheson Colloids, Port Huron, Mich.) was applied to the substrate 110 by flexographic printing. The silver-silver chloride ink contained silver and silver chloride particles (not shown) and formed a silver-silver chloride layer 140 when dried. The thickness of the flexographically printed silver-silver chloride layer 140 was about 0.075 mm. A layer of electrically conductive adhesive (LECTEC 4000 available from Lectec Corp., Minnetonka, Minn.), about 0.2 mm thick, was applied to a portion of the exposed surface of the silver-silver chloride ink layer 140. The boundary of the electrically conductive adhesive layer 150 was spaced inwardly from the edge at the circular end 130 of the substrate 110 and silver-silver chloride layer 140 so that about ⅔ of the surface of the silver-silver chloride layer 140 opposite the substrate was covered by the adhesive. The electrically conductive adhesive layer 150 thus had a smaller surface area than the substrate 110 or the silver-silver chloride layer 140, thereby leaving part of the silver-silver chloride layer 140 exposed. A wired metal clip (not shown) was used to clip onto the portion of the substrate 110 and silver-silver chloride layer 140 that extended outwardly from the electrically conductive adhesive layer 150. The wired clip was connected to a diagnostic system for monitoring the signals received by the electrode 100.

EXAMPLE 2

Electrode

An electrode is made with a process analogous to that of Example 1, except that the substrate is made from a PVP sheet of about 0.1 mm thick. The PVP sheet is made by dissolving PVP of average molecular weight of about 55,000 and K value of about 30 (PVP K-30, Specialty Product International, Lombard, Ill.) in water at about 5 wt % solids, casting on a flat surface and air-drying until a dry solid film of about 0.1 mm thick is formed. The sheet is die-cut into a substrate and an electrode is made therewith in a manner analogous to that in Example 1.

EXAMPLE 3

Electrode

Figure 2:
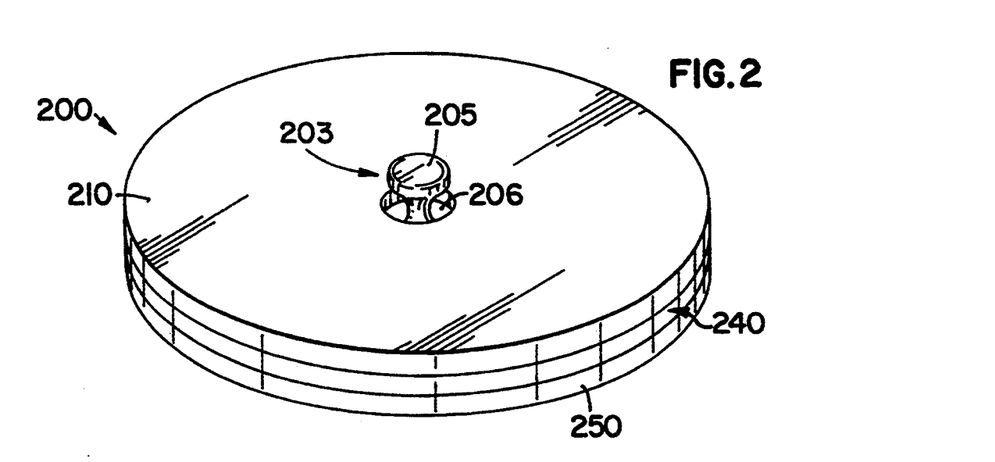
FIG. 2 is an isometric view of another preferred embodiment of a water-degradable electrode.
Figure 3:
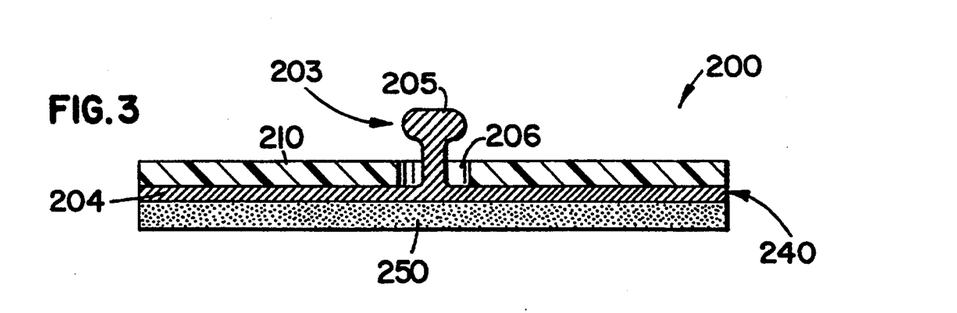
FIG. 3 is a cross-sectional view through the center of the water-degradable electrode of FIG. 2.

Referring to FIG. 2 and FIG. 3, the electrode 200 in this preferred embodiment includes an electrically conductive, silver-silver chloride-coated nylon snap-fastener 203 provided for the conduction of electrical current. The male snap-fastener 203 has a nylon disk member 204 integrally connected to a nylon stud 205. The stud 205 is centrally located on the disk member 204. The nonphotosensitive, electrically conductive, metal-containing layer 240 is formed by brush-painting on the entire male snap-fastener 203 a silver-silver chloride ink, SS-24633 (Acheson Colloids, Port Huron, Mich.) to form a thin silver-silver chloride layer (not shown) having a thickness of about 0.075 mm on the male snap fastener 203. A water-soluble polyvinylpyrrolidone (molecular weight about 55000, K value of about 30) substrate 210 having the same circular dimension (about 2 cm in diameter) as the thin silver-silver chloride-coated layer 240 but having a centrally located hole 206 therein is bonded to the thin silver-silver chloride-coated layer 240. The centrally located hole 206 in the substrate has a diameter that is slightly bigger than the diameter (about 4 mm) of the stud 205 such that when the substrate 210 is bonded to the thin silver-silver chloride-coated layer 240, the stud 205 extends through the hole 206 in the substrate 210 and is exposed. An electrically conductive gel 250 PROMEON RG63B (Promeon Co., Brooklyn Center, Minn.) is disposed on the silver-silver chloride layer 240. The substrate 210, silver-silver chloride layer 240, and the electrically conductive gel 250 all have the same circular dimension. A wired female snap-fastener (not shown) is used to connect the male snap-fastener 203 to a monitoring device.

EXAMPLE 4

Electrode

Figure 4:
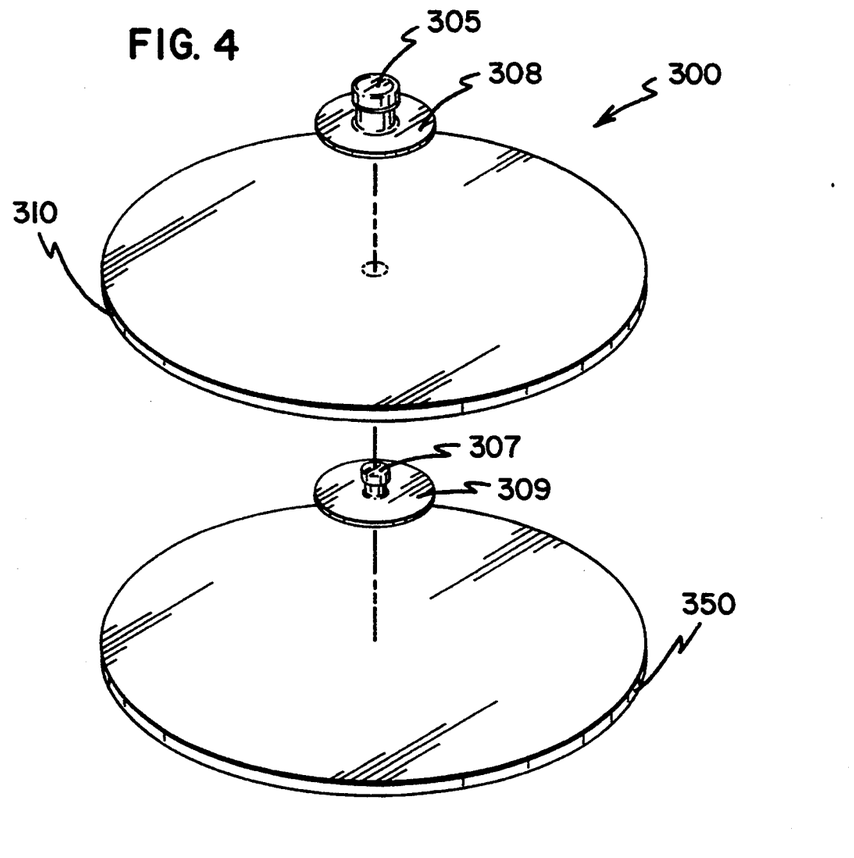
FIG. 4 is an exploded view of another preferred embodiment of a water-degradable electrode of this invention.
Figure 5:
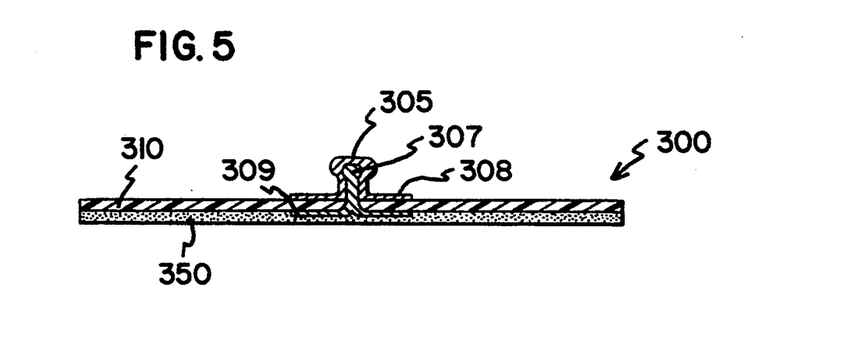
FIG. 5 is a cross-sectional view through the center of the water-degradable electrode of FIG. 4.

Referring to FIG. 4 and FIG. 5, the electrode 300 in this preferred embodiment included a generally circular, water-soluble polyvinyl alcohol (water soluble paper 120FD from Custom Papers Group, Inc. of Richmond, Va.) substrate 310 having a 5 cm diameter and 0.2 mm thickness. The substrate 310 was perforated to form an aperture to receive a silver-silver chloride-coated nylon eyelet (Product No. 107 obtained from Micron Medical Products, Inc., Fitchburg, Mass.) 307, which, extending through the substrate, was pressed into a stainless steel snap-fastener (Product No. BS53052/K1105 obtained from Micron Medical Products, Inc.) 305. The nylon eyelet 307 had a silver-silver chloride layer (not shown) coated. The eyelet 307 had a flat, circular base member 309 of about 1 cm in diameter and the snap-fastener 305 had a flat, circular base member 308 of about 1 cm in diameter. There was electrical continuity between the silver-silver chloride coating on the circular base member 309 of the eyelet and the snap fastener 305. The two aforesaid base members 308 and 309 were disposed on opposite sides of the substrate 310. An electrically conductive gel 350 (LECTEC 4000 available from Lectec Corp., Minnetonka, Minn.) was disposed on the exposed surface of the silver-silver chloride-coated base member 309 of eyelet 307 and on the exposed surface of the substrate 310 on the side opposite to the snap-fastener. A wired female snap-fastener (not shown) was used to connect the snap-fastener 203 to a monitoring device.

EXAMPLE 5

Electrode with Release Liner

An electrode made in Example 4 was protected with a release liner. A sheet of silicone-coated polyester of about 0.25 mm thick was cut to have the same planar dimension (i.e. the same diameter) as that of the adhesive layer to form a disk of release liner. A segment of the adhesive surface facing away from the substrate and on the edge of the adhesive layer defined by an arc of 2 cm long and the corresponding chord was covered with kraft paper. The cut disk of release liner was then laminated onto the exposed adhesive surface by aligning the circumference of the adhesive layer with the circumference of the release liner and pressing the release liner onto the adhesive layer.

EXAMPLE 6

Reclamation of Metal From a Used Electrode

After use, the electrode of Example 1 was immersed in 500 ml of 60° C. water in a beaker and allowed to remain undisturbed until the substrate in the electrode is dissolved. After the dissolution of the substrate, the silver-silver chloride particles were observed to have sunk to the bottom of the beaker. At this time, the pressure sensitive adhesive was partially dissolved. The part of the pressure sensitive adhesive that remained undissolved was picked up and removed from the aqueous solution. The remaining solution was stirred and pumped to a commercially available silver reclaiming system, CYA EFFLUENT TREATMENT SYSTEM 32-04 SBS (CYA Products, Inc., Long Island City, N.Y.) at 60 ml/min to collect the silver-silver chloride particles. The silver-silver chloride particles were later removed from the silver reclaiming system.

EXAMPLE 7

Reclamation of Metal from An Used Electrode

After use, the electrode of Example 4 is immersed in 1000 ml of 25° C. water in a beaker and gently stirred with a stirrer at about 30 rpm. The water is stirred until the substrate and the pressure sensitive adhesive are dissolved. The snap-fastener and the eyelet are retrieved from the aqueous solution and the aqueous solution is then pumped to a commercially available silver reclaiming system, CYA EFFLUENT TREATMENT SYSTEM 32-04 SBS to collect any silver-silver chloride particles that come off the electrode. The silver-silver chloride particles collected in the silver reclaiming system are removed from the reclaiming system later.

The present invention has been described in the foregoing specification. It is to be understood that modifications and alterations of the invention can be made without departing from the spirit and scope of the invention. The embodiments are presented for illustrative purposes only, and are not to be interpreted as limiting the scope of the invention.

What is claimed is:

1. A water-degradable electrode, comprising:
   (a) a water-degradable, electrically nonconductive substrate consisting essentially of water-soluble material; and
   (b) a nonphotosensitive, electrically conductive layer disposed on the nonconductive substrate, said electrically conductive layer comprising a metal or metal alloy.

2. The water-degradable electrode of claim 1 wherein the nonphotosensitive, electrically conductive layer further comprises a nonmetallic, galvanically inactive material.

3. The water-degradable electrode of claim 1 wherein the nonphotosensitive, electrically conductive layer comprises a metal or metal alloy selected from a group consisting of gold, silver, platinum, copper, aluminum, nickel, tin, and stainless steel.

4. The water-degradable electrode of claim 1 wherein the nonphotosensitive, electrically conductive layer comprises silver and silver chloride.

5. The water-degradable electrode of claim 1 wherein the nonphotosensitive, electrically conductive layer comprises a coating containing silver and silver chloride.

6. The water-degradable electrode of claim 5 wherein the coating is silver-silver chloride ink.

7. The water-degradable electrode of claim 1 wherein the water-degradable, electrically nonconductive substrate comprises an enzyme-degradable material.

8. The water-degradable electrode of claim 1 further comprising an electrically conductive pressure sensitive adhesive layer disposed on a side of the nonphotosensitive, electrically conductive layer opposite the substrate.

9. The water-degradable electrode of claim 8 wherein the pressure sensitive adhesive is water-degradable.

10. The water-degradable electrode of claim 1 wherein said electrode is conformable to a contour of a mammalian body to contact the mammalian body and capable of receiving electrical signal from the mammalian body.

11. The water-degradable electrode of claim 1 wherein the nonphotosensitive, electrically conductive layer is flexographically printed on the nonconductive substrate.

12. An electrode assembly, comprising:
   (a) a water-degradable electrically nonconductive substrate consisting essentially of water-soluble material;
   (b) a nonphotosensitive, electrically conductive layer disposed on the nonconductive substrate, said electrically conductive layer comprising a metal or metal alloy;
   (c) an electrically conductive pressure sensitive adhesive layer disposed on a side of the nonphotosensitive, electrically conductive layer opposite the substrate; and
   (d) a release liner releasibly disposed on a side of the pressure sensitive adhesive layer opposite the substrate;

wherein said electrode is conformable to a contour of a mammalian body to contact the mammalian body.

13. The electrode assembly of claim 12 wherein the conductive layer is part of an eyelet that has a stud which extends through the substrate and is pressed into an electrically conductive snap-fastener to provide electrical continuity from the conductive layer to the snap-fastener.

14. An electrode assembly, comprising:
   (a) an electrically nonconductive substrate of polyvinyl alcohol of molecular weight about 100,000 to about 120,000, with a thickness of about 0.1 mm to about 0.2 mm;

(b) a nonphotosensitive, electrically conductive layer disposed on the nonconductive substrate, said electrically conductive layer is silver-silver chloride ink;

(c) a water-degradable electrically conductive pressure sensitive adhesive layer disposed on a side of the nonphotosensitive, electrically conductive layer opposite the substrate; and (d) a release liner releasibly disposed on a side of the pressure sensitive adhesive layer opposite the substrate.

wherein said electrode is conformable to a contour of a mammalian body to contact the mammalian body.

15. A water-degradable electrode, comprising:

(a) a water-degradable, electrically nonconductive substrate; and (b) a nonphotosensitive, electrically conductive layer disposed on the nonconductive substrate, said electrically conductive layer comprising a metal or metal alloy;

wherein the water-degradable, electrically nonconductive substrate comprises polyvinyl alcohol.

16. A water-degradable electrode, comprising:

(a) a water-degradable, electrically nonconductive substrate; and (b) a nonphotosensitive, electrically conductive layer disposed on the nonconductive substrate, said electrically conductive layer comprising a metal or metal alloy;

wherein the water-degradable, electrically nonconductive substrate comprises polyvinylpyrrolidone.

17. A water-degradable electrode, comprising:

(a) a water-degradable, electrically nonconductive substrate; and (b) a nonphotosensitive, electrically conductive layer disposed on the nonconductive substrate, said electrically conductive layer comprising a metal or metal alloy;

wherein the water-degradable, electrically nonconductive substrate comprises a material selected from the group consisting of polypeptide, polylactide, polyglycolide, polycaprolactone, polyvinylpyrrolidone, polyanhydride, polyacrylamide, and any combination thereof.

18. A water-degradable electrode, comprising:

(a) a water-degradable, electrically nonconductive substrate comprising a polymeric material;

(b) a nonphotosensitive, electrically conductive layer disposed on the nonconductive substrate, said electrically conductive layer comprising a metal or metal alloy; and (c) wherein the water-degradable electrically nonconductive substrate will disintegrate in water so that the nonphotosensitive, electrically conductive layer can be separated from the material in the substrate effective for reclaiming of metal or metal alloy of the conductive layer.

19. The water-degradable electrode of claim 18 wherein the water-degradable, electrically nonconductive substrate consists essentially of a homogeneous polymeric material.

20. The water-degradable electrode of claim 18 wherein the polymeric material contains water-soluble thermoplastic polymer.

21. The water-degradable electrode of claim 18 wherein the substrate will disintegrate in water in a few hours.

* * * * *